(12) United States Patent
Chen et al.

(10) Patent No.: US 10,568,919 B2
(45) Date of Patent: Feb. 25, 2020

(54) COMPOSITION FOR LOWERING BLOOD LIPIDS AND USE THEREOF

(71) Applicant: INFINITUS (CHINA) COMPANY LTD., Jiang Men (CN)

(72) Inventors: Zehua Chen, Jiang Men (CN); Jialing Ning, Jiang Men (CN); Chung Wah Ma, Jiang Men (CN); Yiting Yang, Jiang Men (CN); Fang Ma, Jiang Men (CN)

(73) Assignee: INFINITUS (CHINA) COMPANY LTD., Jiang Men (CN)

( * ) Notice: Subject to any disclaimer, the term of this patent is extended or adjusted under 35 U.S.C. 154(b) by 338 days.

(21) Appl. No.: 15/251,076

(22) Filed: Aug. 30, 2016

(65) Prior Publication Data
US 2017/0151296 A1     Jun. 1, 2017

(30) Foreign Application Priority Data
Dec. 1, 2015 (CN) .......................... 2015 1 0870379

(51) Int. Cl.
| | |
|---|---|
| *A61K 36/00* | (2006.01) |
| *A61K 36/185* | (2006.01) |
| *A23L 33/115* | (2016.01) |
| *A61K 31/202* | (2006.01) |
| *A61K 36/02* | (2006.01) |

(52) U.S. Cl.
CPC .......... *A61K 36/185* (2013.01); *A23L 33/115* (2016.08); *A61K 31/202* (2013.01); *A61K 36/02* (2013.01); *A23V 2002/00* (2013.01)

(58) Field of Classification Search
CPC ...................................................... A61K 36/00
USPC .......................................................... 424/725
See application file for complete search history.

(56) References Cited

U.S. PATENT DOCUMENTS

| | | | |
|---|---|---|---|
| 3,859,436 A * | 1/1975 | Jacobi | A61K 8/0212 |
| | | | 514/23 |
| 8,834,857 B1 * | 9/2014 | Winston | A61Q 19/00 |
| | | | 424/401 |
| 2014/0377344 A1 * | 12/2014 | Hershko | A61K 9/19 |
| | | | 424/452 |

* cited by examiner

*Primary Examiner* — Michael V Meller
(74) *Attorney, Agent, or Firm* — Parker Highlander PLLC

(57) ABSTRACT

The present invention discloses a composition and use. The composition comprises hemp seed oil and algal oil with a mass ratio of (20~60):(30~70). After a large number of screening studies on concerted application, the present inventors found that the composition has synergistic effects, specifically, it has significant inhibitory effects on weight gain of animal model rats for hyperlipidemia, can significantly increase the hypolipidemic efficacy, and has an antioxidation effect. In addition, the composition of the present invention has efficacies of improving learning and memory abilities, improving constipation, and protecting the liver. Medicaments and functional food made from the composition of the present invention are simple in production process, stable in product quality, clear in functional factor, prominent in health care efficacy, low in administration dosage, safe in use, without toxic and side effects, and are suitable for consumption of the general population.

7 Claims, No Drawings

COMPOSITION FOR LOWERING BLOOD LIPIDS AND USE THEREOF

CROSS REFERENCE OF RELATED APPLICATION

This application claims the benefit of priority to Chinese Patent Application No. 201510870379.6 filed on Dec. 1, 2015. The entire content of the above-referenced disclosure is specifically incorporated herein by reference.

FIELD

The present invention relates to pharmaceutical field, specifically to a composition and use thereof, and especially to a composition comprising hemp seed oil and algal oil and use thereof.

BACKGROUND

With the continuous improvement of living standards and the unbalanced dietary structure in people's everyday life, excessive finely processed food is consumed and intake of vegetables and fruits are reduced. Meanwhile, exercise is inadequate. Accordingly, the incidence of hyperlipidemia increases year by year. In the recent years, the incidence of atherosclerosis, coronary heart disease, myocardial infarction, hypertension and other cardiovascular and cerebrovascular diseases induced by hyperlipidemia increases year by year, with the morbidity thereof ranking the first place in the total morbidity, which severely jeopardizes the health of human beings. Globally, about 12 million people die of cardiovascular diseases and cerebral stroke every year, and the main cause of coronary heart disease, hypertension and cerebrovascular diseases is atherosclerosis induced by hyperlipidemia.

Hyperlipidemia is a systemic disease, and is referred to as dyslipidemia in the modern medicine. It can be not only caused by genetic and environmental factors, especially improper diet, but also induced by diseases such as diabetes, obesity, and diseases of liver, gallbladder and kidney, etc. Currently, the hypolipidemic ways are mainly (1) rationally adjusting the diet, (2) enhancing the physical exercises, (3) proper physiotherapy including plasma purification therapy, and (4) pharmacotherapy.

Currently, there are mainly four categories of lipid-lowering drugs for treating hyperlipidemia, i.e., statins, fibrates, bile acid sequesterants and nicotinates. The patients need to rationally select hypolipidemic drugs according to different conditions for treatment. However, the majority of synthetic drugs is based on single target mechanism, and is difficult to achieve satisfactory efficacies on modern diseases with complicated etiology such as hyperlipidemia. However, related clinical reports indicate that long-term usage of statins and other chemical hypolipidemic drugs will produce adverse reactions. Therefore, the research and development of novel hypolipidemic drugs have significant social and economical benefits.

SUMMARY

In view of the above, one object of the present invention is to provide a composition.

The composition of the present invention comprises hemp seed oil and algal oil with a mass ratio of (20~60):(30~70).

Hemp seed is the dry ripe fruit of the plant *Cannabis sativa* L. in the Moraceae family. As recorded in "Chinese Pharmacopoeia", it is sweet and calm in nature, and goes to the spleen, the stomach and the large intestine meridians. It has the efficacy of relaxing bowels. It is indicated for blood deficiency & depleted fluid, and intestinal dryness with constipation. In Shennong Bencao Jing, it is classified as top grade, and belongs to a nourishing and moistening Traditional Chinese Medicine (TCM). Moreover, hemp seed is also a common TCM which can be used as both medicine and food. Modern pharmacological studies show that the hemp seed oil mainly contains fatty acids comprising 4.9%~9.5% of saturated fatty acids, and the unsaturated fatty acids therein comprise about 12% of oleic acid, 53% of linoleic acid, 18% of a-linolenic acid, and 3.4% of γ-linolenic acid.

The algal oil is derived from marine microalgae, and obtained by purification of algal species, enlarged culture, extraction of grease, physical refining, and other procedures. The algal oil is rich in polyunsaturated fatty acids, and is an important member in the family of (ω-3 unsaturated fatty acids.

After a large number of screening studies on concerted application, the present inventors found that a combination of hemp seed oil and algal oil in a mass ratio of (20~60):(30~70) has synergistic effects. Specifically, such a combination has significant inhibitory effects on weight gain of animal model rats for hyperlipidemia, can significantly increase the hypolipidemic efficacy, and has an anti-oxidation effect.

As a preference, the mass ratio of the hemp seed oil to the algal oil in the composition of the present invention is (35~60):(35~65).

In some preferred embodiments, the mass ratio of the hemp seed oil to the algal oil in the composition of the present invention is 47:53.

In some other preferred embodiments, the mass ratio of the hemp seed oil to the algal oil in the composition of the present invention is 36:64.

The algal oil in the composition of the present invention comprises EPA.

Preferably, in the algal oil in the composition of the present invention, the content of EPA is 12% or more, and the content of DHA is 24% or more.

In a specific embodiment, through a test for comparing the effects of the hemp seed oil, algal oil and the composition of the present invention on blood lipid and anti-oxidation effect in rats having combined hyperlipidemia in the present invention, it is demonstrated that the composition of the present invention can significantly decrease the body weight, the weigh of orchic fat pad, the weight of perinephric fat pad, fat/body weight ratio, serum TG content, serum TC content, MDA content, and significantly increase the contents of serum HDL-C, SOD, GSH and GSH-Px in rats. In addition, compared to the efficacy of hemp seed oil or algal oil alone, the comprehensive efficacies for decreasing blood lipid and anti-inflammation of the composition of hemp seed oil and algal oil were more potent, suggesting that the composition of hemp seed oil and algal oil of the present invention has synergistic hypolipidemic and anti-inflammatory effects.

In another specific embodiment, through a test for comparing the effects of the hemp seed oil, algal oil and the composition of the present invention on blood lipid and anti-oxidation effect in an animal model of hypercholesterolemia in the present invention, it is demonstrated that the composition of the present invention can significantly decrease the Lee's index, total fat/body weight ratio, serum TG content, serum TC content, MDA content of a rat having hypercholesterolemia, and decrease the increase of adipose tissues surrounding epididymis and kidney as well as the body mass, while the serum HDL-C content and SOD content in rats significantly increase. In addition, compared to the efficacy of hemp seed oil or algal oil alone, the comprehensive efficacies for decreasing blood lipid and anti-inflammation of the composition of hemp seed oil and algal oil were more potent, suggesting that the composition of hemp seed oil and algal oil of the present invention has synergistic hypolipidemic and anti-inflammatory effects. Therefore, the present invention provides use of the composition in the manufacture of a hypolipidemic medicament or functional food.

The present invention also provides a method of lowering blood lipid level, comprising providing the composition as mentioned above.

Through a test for comparing the effects of the hemp seed oil, algal oil and the composition of the present invention on learning and memory abilities in aging model mice induced by D-lactose in the present invention, it is demonstrated that, as compared to hemp seed oil and algal oil, the composition of the present invention can significantly shorten the escape latency in Morris water maze experiment and the time to reach the original platform for the first time, increase the times of crossing the original platform and the sojourn time; prolong the jumping stair latency in the jumping stair experiment and reduce error times; prolong the latency in dark-avoidance test and reduce error times. It is suggested that the efficacy of the composition of hemp seed oil and algal oil of the present invention for increasing the learning and memory abilities are more potent than that of the hemp seed oil or algal oil.

Therefore, the present invention provides use of the composition in the manufacture of a medicament for improving learning and memory abilities.

In a specific embodiment, through a test for comparing the effects of the hemp seed oil, algal oil and the composition of the present invention on laxative function in mice in the present invention, it is demonstrated that the composition of the present invention can shorten the time for the first defecation, increase the amount of defecation, enhance the small intestinal peristalsis, have the efficacies for promoting defecation and increasing the intestinal volume, suggesting that the composition of hemp seed oil and algal oil of the present invention has the efficacy for improving constipation. In addition, with respect to increasing the small intestinal peristalsis, the composition of hemp seed oil and algal oil has a better effect than hemp seed oil or algal oil alone. In other words, the composition of hemp seed oil and algal oil of the present invention has synergistic effect on increasing small intestinal peristalsis.

Therefore, the present invention provides use of the composition in the manufacture of a medicament for improving constipation.

Through a test for comparing the effects of the hemp seed oil, algal oil and the composition of the present invention on liver protection in rats in the present invention, it is demonstrated that, as compared to hemp seed oil and algal oil, the composition of the present invention can significantly decrease the contents of alanine aminotransferase (ALT), aspartate aminotransferase (AST) and malondialdehyde (MDA), significantly increase the content of superoxide dismutase (SOD) in liver tissue, suggesting that the efficacies of the composition of hemp seed oil and algal oil of the present invention for protecting liver cell and decreasing liver damage are more potent than that of hemp seed oil or algal oil.

Therefore, the present invention provides use of the composition in the manufacture of a medicament for protecting liver.

The present invention further provides a pharmaceutical formulation comprising therapeutically effective amount of the composition of the present invention and a pharmaceutically acceptable excipient. Those skilled in the art can directly or indirectly add the composition of the present invention into various pharmaceutically acceptable common excipients required for preparing different dosage forms, such as filler, disintegrant, lubricant, binder, etc., to prepare common formulations such as tablet, capsule, injection, oral liquid, granule, pill, powder and dripping pill, etc. by conventional methods for preparing pharmaceutical formulations. The filler is, e.g., starch, lactose, sucrose, glucose, mannitol, and silicic acid. The disintegrant is, e.g., agar, calcium carbonate, potato starch, tapioca starch, alginic acid, certain silicates, sodium carbonate, and low-substituted hydroxypropyl cellulose. The lubricant is, e.g., talc, calcium sterate, magnesium sterate, solid polyethylene glycol, and sodium lauryl sulfate. The binder is, e.g., carboxymethyl cellulose, alginates, gelatin, polyvinylpyrrolidone, sucrose and arabic gum.

Preferably, the pharmaceutical formulation of the present invention is in the form of tablets, soft capsules, hard capsules, granules or honey ointment.

The composition of the present invention can also be prepared into functional food. The functional food of the present invention comprises a therapeutically effective amount of the composition of the present invention and an acceptable excipient. Functional food refers to food that is suitable for a certain population, has functions for body regulation, does not aim at treating diseases, and does no acute, sub-acute or chronic harm to the human body. The functional food of the present invention can be in the form of ordinary food, and also can be in the form of medicaments, such as hard capsule, soft capsule, tablet, oral liquid, vinum, granule, powder, tea bag, etc.

Preferably, the functional food of the present invention is in the form of tablets, soft capsules, hard capsules, granules or honey ointment.

The present invention provides a composition and use. The composition of the present invention comprises hemp seed oil and algal oil with a mass ratio of (20~60):(30~70). After a large number of screening studies on concerted application, the present inventors found that a combination of hemp seed oil and algal oil in a mass ratio of (20~60):(30~70) has synergistic effects. Specifically, such a combination has significant inhibitory effects on weight gain of animal model rats for hyperlipidemia, can significantly increase the hypolipidemic efficacy, and has an anti-oxidation effect. In addition, the composition of the present invention has efficacies of improving learning and memory abilities, improving constipation, and protecting the liver. Medicaments and functional food made from the composition of the present invention are simple in production process, stable in product quality, clear in functional factor, prominent in health care efficacy, low in administration dosage, safe in use, without toxic and side effects, and are suitable for consumption of the general population.

DETAILED DESCRIPTION

The technical solutions in the examples of the present invention are clearly and completely described in conjunction with the examples of present invention. Obviously, the examples as described are merely a part of examples of the present invention, but not all the examples. All the other examples obtained by those skilled in the art based on the examples of the present invention without creative work are all within the protection scope of the present invention.

In order to further understand the present invention, the present invention is described in detail in conjunction with the examples. Unless particularly described, the contents of the efficacious ingredients of the hemp seed oil are: 10%~25% of a-linolenic acid, 45%~60% of linoleic acid; and the contents of the efficacious ingredients of the algal oil are: 12% or more of EPA, and 24% or more of DHA.

EXAMPLE 1

Effects on Blood Lipid and Anti-oxidation Effect in Rats Having Combined Hyperlipidemia 1. Materials and Methods
1.1 Experimental Animals and Medicaments 70 male Wistar rats, SPF grade, body weight 200±20 g. The quality certificate for experimental animals: No. 420006000000710; License Number: SCXK(E) 2008~0005, provided by Research Center for Experimental animals, Hubei Province.

Test articles: hemp seed oil, algal oil, and low, middle and high dosage groups of composition of hemp seed oil and algal oil (with a mass ratio of 47:53). All the test articles were dissolved in 1 mL polysorbate 80 prior to use, and prepared into suspensions according to the administration volume of 1 mL/100 g rats.

1.2. Experimental Groups and Administration 7 groups in total were arranged in the experiment: blank control group, model control group, hemp seed oil group (320 mg/kg), algal oil group (320 mg/kg), low dosage group (160 mg/kg) of the composition of hemp seed oil and algal oil (with a mass ratio of 47:53), middle dosage group (320 mg/kg) of the composition of hemp seed oil and algal oil (with a mass ratio of 47:53), and high dosage group (640 mg/kg) of the composition of hemp seed oil and algal oil (with a mass ratio of 47:53).

1.3. Experimental Method

It the present experiment, 20.0% sucrose, 15% lard, 1.2% cholesterol, 0.2% sodium cholate, appropriate amount of casein, calcium hydrogen phosphate, mountain flour, etc. were added into the sustaining feed. The water, crude protein, crude fiber, crude ash, calcium and phosphorus should all meet the national standard of the sustaining feed except crude fat.

Rats were fed with sustaining feed and observed for 5 days, and were randomly divided into 2 groups based on body weight. 10 rats were administered with the sustaining feed as the blank control group, and 60 rats were administered with model feed as the model control group. The body weight was weighed once every week. 2 weeks after the model control group was administered with the model feed, blood was collected (ocular medial canthus) from the rats in the blank control group and the model control group without fasting, and after that serum was separated as soon as possible so as to test the TC, TG, LDL-C and HDL-C levels in the serum. The model group was randomly divided into 6 groups based on TC level. After the division of groups, there was no significant difference among various model control groups in respect of TC, TG, LDL-C and HDL-C levels. After the division of groups, the test articles were intragastrically administered for 3 consecutive weeks. The blank control group and model control group were simultaneously intragastrically administered with equal volume of distilled water. The blank control group was continuously administered with the sustaining food, while the model control group and each administration group were continuously administered with the model feed. The body weight was weighed regularly. After the experiment was finished, blood was collected without fasting, and after that serum was separated as soon as possible so as to determine the TC, TG, LDL-C and HDL-C levels in the serum. The content of serum malondialdehyde (MDA), the activity of superoxide dismutase (SOD), the content of glutathione (GSH), and the activity of glutathione peroxidase (GSH-Px) were determined. Body weights of the experimental animals were observed. The epididymal fat pad and perinephric fat pad were peeled off, placed on a filter paper to absorb the tissue fluid, weighed, and calculation for fat/body weight ratio was conducted according to the following formula: fat/body weight ratio=(weight of the epididymal fat pad+weight of the perinephric fat pad)/body weight×100%.

1.4. Data Processing

The measurement data were expressed by $\bar{x}\pm s$ and analyzed by SPSS19.0 statistical software. T-test was employed for intergroup comparison, and $P<0.05$ indicates that the difference is statistically significant.

2. Experimental Results 2.1. Comparison of Body Weight, Body Weight Gain and Fat/Body Weight Ratio Among Various Groups of Rats

TABLE 1

Comparison of body weight, weight of epididymal fat pad, weight of perinephric fat pad, fat/body weight ratio among various groups ($\bar{x}\pm s$, n = 10)

| Groups | Dosage (mg/kg) | Body weight (g) | Weight of epididymal fat pad (g) | Weight of perinephric fat pad (g) | Fat/body weight ratio |
|---|---|---|---|---|---|
| Blank control group | — | 365.24 ± 32.61 | 5.12 ± 1.06 | 7.01 ± 1.28 | 3.09 ± 0.62 |
| Model control group | — | 429.13 ± 31.05 ** | 9.04 ± 2.03 ** | 11.51 ± 4.07 ** | 4.68 ± 0.81* |
| Hemp seed oil group | 320 | 386.7 ± 14.79▲▲ | 5.04 ± 0.75▲▲ | 5.35 ± 1.57▲▲ | 2.75 ± 0.84▲▲ |
| Algal oil group | 320 | 410.35 ± 27.09▲ | 7.04 ± 0.98▲ | 7.83 ± 3.06▲▲ | 3.62 ± 0.64▲ |
| Low dosage group of the composition of hemp seed | 160 | 390.71 ± 20.42▲▲ | 5.64 ± 1.83▲▲ | 7.25 ± 1.96▲▲ | 3.12 ± 0.75▲ |

TABLE 1-continued

Comparison of body weight, weight of epididymal fat pad, weight of perinephric fat pad, fat/body weight ratio among various groups ($\bar{x} \pm s$, n = 10)

| Groups | Dosage (mg/kg) | Body weight (g) | Weight of epididymal fat pad (g) | Weight of perinephric fat pad (g) | Fat/body weight ratio |
|---|---|---|---|---|---|
| oil and algal oil | | | | | |
| Middle dosage group of the composition of hemp seed oil and algal oil | 320 | 388.94 ± 31.25▲▲ | 5.43 ± 1.69▲▲ | 6.78 ± 2.61▲▲ | 2.93 ± 0.71▲▲ |
| High dosage group of the composition of hemp seed oil and algal oil | 640 | 386.83 ± 30.34▲▲ | 5.25 ± 1.98▲▲ | 5.67 ± 2.45▲▲ | 2.90 ± 0.70▲▲ |

Notes:
in comparison with the blank control group, ★P < 0.05, ★★ P < 0.01; in comparison with the model control group, ▲ P < 0.05, ▲▲P < 0.01.

Results in Table 1 indicate that, as compared to the blank control group, the body weight, weight of epididymal fat pad, the weight of perinephric fat pad, fat/body weight ratio of rats in the model control group significantly increase (P<0.01 or P<0.05), suggesting successful replication of the animal model for hyperlipidemia. As compared to the model control group, the body weight, weight of epididymal fat pad, weight of perinephric fat pad and fat/body weight ratio of rats in the high, middle and low dosage groups of the composition of hemp seed oil and algal oil (with a mass ratio of 47:53) significantly decrease (P<0.01 or P<0.05); the body weight, the weight of epididymal fat pad, the weight of perinephric fat pad, fat/body weight ratio of rats in the group of hemp seed oil monotherapy significantly decrease (P<0.01); the body weight, the weight of epididymal fat pad, the weight of perinephric fat pad, fat/body weight ratio of rats in the group of algal oil monotherapy significantly decrease (P<0.01 or P<0.05). It is suggested that the hemp seed oil group and the group of the composition of hemp seed oil and algal oil (with a mass ratio of 47:53) have significant inhibitory effects on weight gain of the animal model for hyperlipidemia in rats, and the effects of inhibiting the weight gain of the animal model for hyperlipidemia in rats in the hemp seed oil group and the group of the composition of hemp seed oil and algal oil (with a mass ratio of 47:53) are significantly better than that of the algal oil group.

2.2. Comparison of Biochemical Indicators for Blood Lipid Among Various Groups of Rats

TABLE 2

Comparison of biochemical indicators for blood lipid among various groups ($\bar{x} \pm s$, n = 10)

| Groups | Dosage (mg/kg) | TC (mmol/l) | TG (mmol/l) | LDL-C (mmol/l) | HDL-C (mmol/l) |
|---|---|---|---|---|---|
| Blank control group | — | 1.24 ± 0.27 | 0.72 ± 0.21 | 0.55 ± 0.12 | 1.26 ± 0.07 |
| Model control group | — | 1.95 ± 0.26★ | 1.13 ± 0.23★★ | 0.65 ± 0.05 | 1.13 ± 0.05★★ |
| Hemp seed oil group | 320 | 2.04 ± 0.44 | 0.83 ± 0.12▲ | 0.69 ± 0.43 | 1.20 ± 0.71▲ |
| Algal oil group | 320 | 1.49 ± 0.21▲ | 0.77 ± 0.14▲▲ | 0.61 ± 0.13 | 1.23 ± 0.32▲ |
| Low dosage group of the composition of hemp seed oil and algal oil | 160 | 1.53 ± 0.14▲ | 0.88 ± 0.24▲ | 0.60 ± 0.03 | 1.22 ± 0.05▲ |
| Middle dosage group of the composition of hemp seed oil and algal oil | 320 | 1.51 ± 0.15▲ | 0.79 ± 0.16▲▲ | 0.59 ± 0.05 | 1.30 ± 0.06▲▲ |
| High dosage group of the composition of hemp seed oil and algal oil | 640 | 1.38 ± 0.16▲▲ | 0.72 ± 0.12▲▲ | 0.58 ± 0.06 | 1.32 ± 0.05▲▲ |

Notes:
in comparison with the blank control group, ★P < 0.05, ★★P < 0.01; in comparison with the model control group, ▲P < 0.05, ▲▲P < 0.01.

Results in Table 2 indicate that, as compared to the blank control group, in the serum of rats in the model control group, the contents of TG and TC significantly increase, and the content of HDL-C significantly decreases (P<0.01 or P<0.05). As compared to the model control group, in the serum of rats in the high, middle and low dosage groups of the composition of hemp seed oil and algal oil (with a mass ratio of 47:53), the contents of TG and TC significantly decrease, and the content of HDL-C significantly increases (P<0.01 or P<0.05); in the serum of rats in hemp seed oil group, the content of TG significantly decreases, and the content of HDL-C significantly increases (P<0.05); in the serum of rats in algal oil group, the contents of TG and TC significantly decrease, and the content of HDL-C significantly increases (P<0.01 or P<0.05). The above results indicate that the hemp seed oil group, the algal oil group and the groups of the composition of hemp seed oil and algal oil (with a mass ratio of 47:53) all have certain hypolipidemic effects in rats of the animal model for hyperlipidemia. From the results of decreased TC and TG contents as well as increased HDL-C content for various test articles, it is known that the middle dosage group (320 mg/kg) of the composition of hemp seed oil and algal oil has a significantly better hypolipidemic effect than the group of hemp seed oil monotherapy (320 mg/kg) and the group of algal oil monotherapy (320 mg/kg). It is suggested that group of the composition of hemp seed oil and algal oil (with a mass ratio of 47:53) has synergistic hypolipidemic effect in rats of the animal model for hyperlipidemia.

2.3 Effects on Activities of MDA, SOD, GSH and GSH-Px in Various Groups of Rats hemp seed oil, algal oil and the composition of hemp seed oil and algal oil (with a mass ratio of 47:53) have a certain anti-oxidation effect in rats of animal model for hyperlipidemia. When the anti-oxidation effects of the monotherapies are compared to those of the compounded compositions, the anti-oxidation effect of the groups of the composition of hemp seed oil and algal oil (with a mass ratio of 47:53) are significantly better than that of the group of hemp seed oil monotherapy and the group of algal oil monotherapy. In other words, the composition of hemp seed oil and algal oil (with a mass ratio of 47:53) has synergistic anti-oxidation effect.

EXAMPLE 2

Effects on Blood Lipid and Anti-oxidation Effect in Animal Model for Hypercholesterolemia 1. Materials and Methods 1.1. Experimental Animals and Medicaments 70 male Wistar rats, SPF grade, body weight 200±20 g. The quality certificate for experimental animals: No. 420006000000710; License Number: SCXK(E) 2008~0005, provided by Research Center for Experimental animals, Hubei Province.

Test articles: hemp seed oil, algal oil, and low, middle and high dosage groups of composition of hemp seed oil and

TABLE 3

Comparison of activities of MDA, SOD, GSH and GSH-Px in various groups ($\bar{x}\pm s$, n = 10)

| Groups | Dosage (mg/kg) | MDA (nmol/mL) | SOD (U/mL) | GSH (nmol/mg) | GSH-Px (U/mg) |
|---|---|---|---|---|---|
| Blank control group | — | 6.56 ± 0.76 | 135.83 ± 21.26 | 19.23 ± 0.71 | 118.71 ± 4.16 |
| Model control group | — | 13.63 ± 1.13★ | 86.76 ± 17.72★★ | 13.66 ± 0.48★★ | 83.16 ± 2.72★★ |
| Hemp seed oil group | 320 | 8.84 ± 1.45▲ | 92.42 ± 31.27▲ | 13.75 ± 0.32 | 101.36 ± 2.79▲ |
| Algal oil group | 320 | 8.20 ± 1.29▲ | 97.14 ± 27.34▲ | 15.87 ± 0.75▲ | 95.31 ± 5.01▲ |
| Low dosage group of the composition of hemp seed oil and algal oil | 160 | 8.98 ± 0.94▲ | 96.64 ± 20.83▲ | 15.46 ± 0.51▲ | 96.64 ± 3.13▲ |
| Middle dosage group of the composition of hemp seed oil and algal oil | 320 | 8.62 ± 0.82▲ | 101.03 ± 21.69▲▲ | 16.73 ± 0.54▲ | 105.48 ± 3.49▲ |
| High dosage group of the composition of hemp seed oil and algal oil | 640 | 7.25 ± 0.75▲ | 103.22 ± 19.86▲▲ | 18.12 ± 0.66▲▲ | 112.12 ± 3.46▲▲ |

Notes:
in comparison with the blank control group, ★P < 0.05, ★★P < 0.01; in comparison with the model control group, ▲P < 0.05, ▲▲P < 0.01.

Results in Table 3 indicate that, as compared to the blank control group, in the rats of the model control group, the content of MDA significantly increases, and the contents of SOD, GSH and GSH-Px significantly decrease (P<0.01). As compared to the model control group, in the rats of the high, middle and low dosage groups of the composition of hemp seed oil and algal oil (with a mass ratio of 47:53), the content of MDA significantly decreases, and the contents of SOD, GSH and GSH-Px significantly increase (P<0.01 or P <0.05); in the rats of the hemp seed oil group, the content of MDA significantly decreases, and the contents of SOD and GSH-Px significantly increase (P<0.05); in the rats of the algal oil group, the content of MDA significantly decreases, and the contents of SOD, GSH and GSH-Px significantly increase (P<0.05). The results suggest that the groups of algal oil (with a mass ratio of 36:64). All the test articles were dissolved in 1 mL polysorbate 80 prior to use, and prepared into suspensions according to the administration volume of 1 mL/100 g rats.

1.2. Experimental Groups and Administration 7 groups in total were arranged in the experiment: blank control group, model control group, hemp seed oil group (170 mg/kg), algal oil group (170 mg/kg), low dosage group (85 mg/kg) of the composition of hemp seed oil and algal oil (with a mass ratio of 36:64), middle dosage group (170 mg/kg) of the composition of hemp seed oil and algal oil (with a mass ratio of 36:64), and high dosage group (340 mg/kg) of the composition of hemp seed oil and algal oil (with a mass ratio of 36:64).

1.3. Experimental Method

The high cholesterol feed employed in the present experiments consists of 88.7% of ordinary murine feed, 1% of cholesterol, 10% of lard and 0.3% of sodium cholate. The water, crude protein, crude fat, crude fiber, crude ash, calcium and phosphorus of the model feed should all meet the national standard of the sustaining feed.

Rats were fed with sustaining feed and observed for 5 days, and were randomly divided into 2 groups based on body weight. 10 rats were administered with the sustaining feed as the blank control group, and 60 rats were administered with model feed as the model control group. The body weight was weighed once every week. 2 weeks after the model control group was administered with the model feed, blood was collected (ocular medial canthus) from the rats in the blank control group and the model control group without fasting, and after that serum was separated as soon as possible so as to test the TC, TG, LDL-C and HDL-C levels in the serum. The model group was randomly divided into 6 groups based on TC level. After the division of groups, there was no significant difference among various model control groups in respect of TC, TG, LDL-C and HDL-C levels. After the division of groups, the test articles were intragastrically administered for 3 consecutive weeks. The blank control group and model control group were simultaneously intragastrically administered with equal volume of distilled water. The blank control group was continuously administered with the sustaining food, while the model control group and each administration group were continuously administered with the model feed. The body weight was weighed regularly. After the experiment was finished, blood was collected without fasting, and after that serum was separated as soon as possible so as to determine the TC, TG, LDL-C and HDL-C levels in the serum. The contents of serum and liver malondialdehyde (MDA) and the activity of superoxide dismutase (SOD) were determined. The rats were anesthetized by 3% pentobarbital sodium, and the body length thereof was measured to calculate Lee's index. The liver, adipose tissues surrounding the kidney and epididymis were collected and weighed.

1.4. Data Processing

The measurement data were expressed by $\bar{x}\pm s$ and analyzed by SPSS19.0 statistical software. T-test was employed for intergroup comparison, and $P<0.05$ indicates that the difference is statistically significant.

2. Experimental Results

2.1. Comparison of Body Mass, Lee's Index and Fat/Body Weight Ratio Among Various Groups of Rats

TABLE 4

Comparison of body mass, Lee's index and fat/body weight ratio among various groups of rats ($\bar{x}\pm s$, n = 10)

| Groups | Dosage (mg/kg) | Weight gain (g/d) | Lee's index | Kidney fat/body weight ratio (mg/g) | epididymis fat/body weight ratio (mg/g) | Total fat/body weight ratio (mg/g) |
|---|---|---|---|---|---|---|
| Blank control group | — | 3.47 ± 0.24 | 2.91 ± 0.03 | 1.97 ± 0.08 | 11.32 ± 0.27 | 13.27 ± 0.31 |
| Model control group | — | 4.23 ± 0.15 ★★ | 3.11 ± 0.04 ★ | 2.95 ± 0.10 ★★ | 14.65 ± 0.26 ★★ | 17.61 ± 0.23 ★★ |
| Hemp seed oil group | 170 | 3.75 ± 0.36 ▲ | 2.95 ± 0.01 ▲ | 2.74 ± 0.11 ▲ | 13.51 ± 0.15 ▲ | 16.10 ± 0.31 ▲ |
| Algal oil group | 170 | 3.91 ± 0.11 | 3.04 ± 0.04 | 2.89 ± 0.08 | 14.20 ± 0.37 | 17.02 ± 0.55 |
| Low dosage group of the composition of hemp seed oil and algal oil | 85 | 4.03 ± 0.21 | 3.09 ± 0.03 | 2.91 ± 0.11 | 14.32 ± 0.28 | 17.12 ± 0.24 |
| Middle dosage group of the composition of hemp seed oil and algal oil | 170 | 3.59 ± 0.14 ▲ | 2.98 ± 0.03 ▲ | 2.61 ± 0.12 ▲ | 13.31 ± 0.42 ▲ | 15.95 ± 0.41 ▲ |
| High dosage group of the composition of hemp seed oil and algal oil | 340 | 3.26 ± 0.11 ▲▲ | 2.93 ± 0.03 ▲ | 2.43 ± 0.09 ▲▲ | 12.08 ± 0.30 ▲▲ | 14.31 ± 0.36 ▲▲ |

Notes:
in comparison with the blank control group, ★ P < 0.05, ★★ P < 0.01; in comparison with the model control group, ▲ P < 0.05, ▲▲ P < 0.01.

The results in Table 4 indicate that, as compared to normal groups, the body mass and Lee's index of rats in the model control group significantly increase, and adipose tissues surrounding kidney and epididymis significantly increases (P<0.01 or P<0.05). As compared to the model control group, each of the hemp seed oil group and the middle and high dosage groups of the composition of hemp seed oil and algal oil (with a mass ratio of 36:64) can significantly decrease the Lee's index and total fat/body weight ratio of the rats having hypercholesterolemia, and decrease the increase of the adipose tissues surrounding epididymis (P<0.01 or P<0.05). The middle and high dosage groups of the composition of hemp seed oil and algal oil (with a mass ratio of 36:64) have significant effects of reducing the increase of body mass and adipose tissues surrounding kidney, and decreasing the total fat/body weight ratio of the rats having hypercholesterolemia (P<0.01 or P<0.05). The hemp seed oil group and the middle dosage group of the composition of hemp seed oil and algal oil (with a mass ratio of 36:64) are both better in inhibiting various indicators such as increase of adipose and body weigh of rats having hypercholesterolemia than the algal oil group.

2.2 Effects on Biochemical Indicators of Blood Lipid Among Various Groups of Rats

TABLE 5

Comparison of biochemical indicators of blood lipid among various groups ($\bar{x} \pm s$, n = 10)

| Groups | Dosage (mg/kg) | TC (mmol/l) | TG (mmol/l) | LDL-C (mmol/l) | HDL-C (mmol/l) |
|---|---|---|---|---|---|
| Blank control group | — | 1.44 ± 0.07 | 0.95 ± 0.03 | 0.56 ± 0.13 | 1.27 ± 0.06 |
| Model control group | — | 2.32 ± 0.06★ | 1.52 ± 0.04★★ | 0.92 ± 0.06★★ | 1.12 ± 0.05★★ |
| Hemp seed oil group | 170 | 2.35 ± 0.13 | 1.43 ± 0.07 | 0.71 ± 0.08▲ | 1.13 ± 0.08 |
| Algal oil group | 170 | 1.97 ± 0.03▲ | 1.38 ± 0.10▲ | 0.61 ± 0.04▲▲ | 1.19 ± 0.12▲ |
| Low dosage group of the composition of hemp seed oil and algal oil | 85 | 2.23 ± 0.07 | 1.46 ± 0.05 | 0.81 ± 0.04 | 1.15 ± 0.06 |
| Middle dosage group of the composition of hemp seed oil and algal oil | 170 | 2.02 ± 0.11▲ | 1.36 ± 0.04▲ | 0.62 ± 0.05▲▲ | 1.28 ± 0.05▲▲ |
| High dosage group of the composition of hemp seed oil and algal oil | 340 | 1.85 ± 0.07▲ | 1.23 ± 0.04▲▲ | 0.60 ± 0.07▲▲ | 1.29 ± 0.04▲▲ |

Notes:
in comparison with the blank control group, ★P < 0.05, ★★P < 0.01; in comparison with the model control group, ▲P < 0.05, ▲▲P < 0.01.

The results in Table 5 indicate that, as compared to the blank control group, in the serum of rats in the model control group, the contents of TG and TC significantly increase, the content of HDL-C significantly decreases, and the content of LDL-C significantly increases (P<0.01 or P<0.05). As compared to the model control group, in the serum of rats in the middle and high dosage groups of the composition of hemp seed oil and algal oil (with a mass ratio of 36:64), the contents of TC, TG and LDL-C significantly decrease, and the content of HDL-C significantly increases (P<0.01 or P<0.05); in the serum of rats in hemp seed oil group, the content of LDL-C significantly decreases (P<0.05); in the serum of rats in algal oil group, the contents of TC, TG and LDL-C significantly decrease, and the content of HDL-C significantly increases (P<0.01 or P<0.05). The above results indicate that each of the algal oil group, and the groups of the composition of hemp seed oil and algal oil (with a mass ratio of 36:64) has a certain hypolipidemic effects in rats of the animal model for hypercholesterolemia. As compared to the model control group, the algal oil group and the middle dosage group of the composition of hemp seed oil and algal oil (with a mass ratio of 36:64) are comparable in reducing the contents of TC, TG and LDL-C in serum of rats of animal model for hypercholesterolemia. With respect to the effect of increasing the HDL-C level, the groups of the composition of hemp seed oil and algal oil are better than the algal oil group, i.e. the composition of hemp seed oil and algal oil (with a mass ratio of 36:64) has synergistic effect on the hypolipidemic efficacy in rats of animal model for hypercholesterolemia.

2.3 Effects on MDA and SOD Among Various Groups of Rats

TABLE 6

Comparison of MDA and SOD among various groups ($\bar{x} \pm s$, n = 10)

| Groups | Dosage (mg/kg) | Serum MDA (nmol/ml) | Serum SOD (U/ml) | Liver MDA (nmol/ml) | Liver SOD (U/ml) |
|---|---|---|---|---|---|
| Blank control group | — | 7.37 ± 0.98 | 174.13 ± 20.06 | 6.58 ± 0.79 | 241.63 ± 28.41 |
| Model control group | — | 8.95 ± 1.44★ | 106.56 ± 40.72★★ | 13.68 ± 1.14★★ | 203.21 ± 40.02★ |
| Hemp seed oil group | 170 | 8.51 ± 1.03 | 149.83 ± 53.08▲ | 10.32 ± 0.52▲ | 231.12 ± 24.35▲▲ |
| Algal oil group | 170 | 6.15 ± 1.31▲▲ | 159.36 ± 34.27▲ | 9.01 ± 1.75▲▲ | 228.32 ± 23.90▲ |
| Low dosage group of the composition of hemp seed oil and algal oil | 85 | 8.73 ± 1.12 | 115.34 ± 47.73 | 12.43 ± 1.82 | 210.74 ± 16.81 |
| Middle dosage group of the composition of hemp seed oil and algal oil | 170 | 6.23 ± 0.91▲▲ | 154.03 ± 48.69▲ | 8.62 ± 0.83▲▲ | 227.18 ± 17.59▲ |

TABLE 6-continued

Comparison of MDA and SOD among various groups ($\bar{x} \pm s$, n = 10)

| Groups | Dosage (mg/kg) | Serum MDA (nmol/ml) | Serum SOD (U/ml) | Liver MDA (nmol/ml) | Liver SOD (U/ml) |
|---|---|---|---|---|---|
| High dosage group of the composition of hemp seed oil and algal oil | 340 | 5.74 ± 1.01▲▲ | 171.12 ± 29.76▲▲ | 7.39 ± 0.74▲▲ | 235.14 ± 19.76▲▲ |

Notes:
in comparison with the blank control group, *P < 0.05, **P < 0.01; in comparison with the model control group, ▲P < 0.05, ▲▲P < 0.01.

From the results in Table 6, it can be found that the MDA levels in both serum and liver of the model control group are higher than those of the blank control group, while the activities of SOD are lower, with significant differences (P <0.01 or P<0.05). As compared to the model control group, in the middle and high dosage groups of the composition of hemp seed oil and algal oil (with a mass ratio of 36:64), the content of MDA significantly decreases, and the content of SOD significantly increases (P<0.01 or P<0.05); in the rats of hemp seed oil group, the content of liver MDA significantly decreases, and the SOD levels in serum and liver significantly increase (P<0.01 or P<0.05); in the rats of algal oil group, the content of MDA significantly decreases, and the content of SOD significantly increases (P<0.01 or P<0.05). The results suggest that the hemp seed oil group, the algal oil group and groups of the composition of hemp seed oil and algal oil (with a mass ratio of 36:64) have anti-oxidation effect.

EXAMPLE 3

Studies on the Hypolipidemic and Anti-oxidation Effects in Rats Having Combined Hyperlipidemia 1. Materials and Methods
1.1. Experimental Animals and Medicaments
70 male Wistar rats, SPF grade, body weight 200±20 g. The quality certificate for experimental animals: No. 420006000000710; License Number: SCXK(E) 2008~0005, provided by Research Center for Experimental animals, Hubei Province.
Test articles: Hemp seed oil, algal oil, and low, middle and high dosage groups of composition of hemp seed oil and algal oil (with a mass ratio of 63:37). All the test articles were dissolved in 1 mL polysorbate 80 prior to use, and prepared into suspensions according to the administration volume of 1 mL/100 g rats.
1.2. Experimental Groups 7 groups in total were arranged: blank control group, model control group, hemp seed oil group (340 mg/kg), algal oil group (340 mg/kg), low dosage group (170 mg/kg) of the composition of hemp seed oil and algal oil (with a mass ratio of 63:37), middle dosage group (340 mg/kg) of the composition of hemp seed oil and algal oil (with a mass ratio of 63:37), and high dosage group (510 mg/kg) of the composition of hemp seed oil and algal oil (with a mass ratio of 63:37).
1.3. Experimental Method
It the present experiment, 20.0% sucrose, 15% lard, 1.2% cholesterol, 0.2% sodium cholate, appropriate amount of casein, calcium hydrogen phosphate, mountain flour, etc. were added into the sustaining feed. The water, crude protein, crude fiber, crude ash, calcium and phosphorus should all meet the national standard of the sustaining feed except crude fat.
Rats were fed with sustaining feed and observed for 5 days, and were randomly divided into 2 groups based on body weight. 10 rats were administered with the sustaining feed as the blank control group, and 60 rats were administered with model feed as the model control group. The body weight was weighed once every week. 2 weeks after the model control group was administered with the model feed, blood was collected (ocular medial canthus) from the rats in the blank control group and the model control group without fasting, and after that serum was separated as soon as possible so as to test the TC, TG, LDL-C and HDL-C levels in the serum. The model control group was randomly divided into 6 groups based on TC level. After the division of groups, there was no significant difference among various model control groups in respect of TC, TG, LDL-C and HDL-C levels. After the division of groups, the test articles were intragastrically administered for 3 consecutive weeks. The blank control group and model control group were simultaneously intragastrically administered with equal volume of distilled water. The blank control group was continuously administered with the sustaining food, while the model control group and each administration group were continuously administered with the model feed. The body weight was weighed regularly. After the experiment was finished, blood was collected without fasting, and after that serum was separated as soon as possible so as to determine the TC, TG, LDL-C and HDL-C levels in the serum. The content of serum malondialdehyde (MDA), the activity of superoxide dismutase (SOD), the content of glutathione (GSH), and the activity of glutathione peroxidase (GSH-Px) were determined. Body weights of the experimental animals were observed. The epididymal fat pad and perinephric fat pad were peeled off, placed on a filter paper to absorb the tissue fluid, weighed, and calculation for fat/body weight ratio was conducted according to the following formula: fat/body weight ratio=(weight of the epididymal fat pad+ weight of the perinephric fat pad)/body weight×100%.
1.4. Data Processing
The measurement data were expressed by $\bar{x} \pm s$ and analyzed by SPSS19.0 statistical software. T-test was employed for intergroup comparison, and P<0.05 indicates that the difference is statistically significant.
2. Experimental Results
2.1. Comparison of Body Weight, Weight of Epididymal Fat Pad, Weight of Perinephric Fat Pad and Fat/Body Weight Ratio Among Various Groups of Rats

TABLE 7

Comparison of body weight, weight of epididymal fat pad, weight of perinephric fat pad and fat/body weight ratio among various groups ($\bar{x} \pm s$, n = 10)

| Groups | Dosage (mg/kg) | Body weight (g) | Weight of epididymal fat pad (g) | Weight of perinephric fat pad (g) | Fat/body weight ratio |
|---|---|---|---|---|---|
| Blank control group | — | 364.19 ± 32.58 | 5.11 ± 1.12 | 7.14 ± 1.31 | 3.06 ± 0.59 |
| Model control group | — | 430.24 ± 30.97★★ | 9.35 ± 1.98★★ | 12.49 ± 2.13★★ | 4.71 ± 0.81★ |
| Hemp seed oil group | 340 | 390.53 ± 36.14▲▲ | 5.52 ± 1.34▲▲ | 7.19 ± 0.97▲▲ | 3.24 ± 0.65▲ |
| Algal oil group | 340 | 415.73 ± 27.18▲ | 7.02 ± 1.55▲ | 9.32 ± 1.48▲ | 4.03 ± 1.06 |
| Low dosage group of the composition of hemp seed oil and algal oil | 170 | 392.65 ± 22.34▲▲ | 5.58 ± 1.92▲▲ | 7.37 ± 1.85▲▲ | 3.14 ± 0.78▲ |
| Middle dosage group of the composition of hemp seed oil and algal oil | 340 | 389.88 ± 31.29▲▲ | 5.46 ± 1.71▲▲ | 6.72 ± 1.93▲▲ | 2.95 ± 0.73▲▲ |
| High dosage group of the composition of hemp seed oil and algal oil | 510 | 385.12 ± 30.52▲▲ | 5.18 ± 1.85▲▲ | 5.97 ± 1.85▲▲ | 2.91 ± 0.72▲▲ |

Notes:
in comparison with the blank control group, ★P < 0.05, ★★P < 0.01; in comparison with the model control group, ▲P < 0.05, ▲▲P < 0.01.

The results in Table 7 indicate that, as compared to the blank control group, the body weight, weight of epididymal fat pad, weight of perinephric fat pad and fat/body weight ratio of rats in the model control group significantly increase (P<0.01 or P<0.05), suggesting successful replication of the animal model for hyperlipidemia. As compared to the model control group, the body weight, weigh of epididymal fat pad, weight of perinephric fat pad and fat/body weight ratio of rats in the high, middle and low dosage groups of the composition of hemp seed oil and algal oil (with a mass ratio of 63:37) significantly decrease (P<0.01 or P<0.05); the body weight, weight of epididymal fat pad, weight of perinephric fat pad of rats in the algal oil group significantly decrease (P<0.05). It is suggested that the hemp seed oil group, algal oil group and the groups of the composition of hemp seed oil and algal oil (with a mass ratio of 63:37) have significant inhibitory effects on weight gain of animal model rats for hyperlipidemia, and the effects of inhibiting the weight gain of animal model rats for hyperlipidemia in the groups of the composition of hemp seed oil and algal oil (with a mass ratio of 63:37) are significantly better than that of the algal oil group.

2.2 Comparison of Biochemical Indicators for Blood Lipid Among Various Groups of Rats

TABLE 8

Comparison of biochemical indicators for blood lipid among various groups ($\bar{x} \pm s$, n = 10)

| Groups | Dosage (mg/kg) | TC (mmol/l) | TG (mmol/l) | LDL-C (mmol/l) | HDL-C (mmol/l) |
|---|---|---|---|---|---|
| Blank control group | — | 1.23 ± 0.26 | 0.73 ± 0.24 | 0.54 ± 0.13 | 1.31 ± 0.08 |
| Model control group | — | 1.93 ± 0.27★ | 1.16 ± 0.25★★ | 0.62 ± 0.06 | 1.12 ± 0.04★★ |
| Hemp seed oil group | 340 | 1.89 ± 0.18 | 0.88 ± 0.20▲ | 0.63 ± 0.12 | 1.23 ± 0.03▲ |
| Algal oil group | 340 | 1.52 ± 0.24▲ | 0.81 ± 0.16▲▲ | 0.60 ± 0.08 | 1.22 ± 0.07▲ |
| Low dosage group of the composition of hemp seed oil and algal oil | 170 | 1.52 ± 0.15▲ | 0.89 ± 0.23▲ | 0.61 ± 0.04 | 1.24 ± 0.06▲ |
| Middle dosage group of the composition of hemp seed oil and algal oil | 340 | 1.51 ± 0.17▲ | 0.82 ± 0.17▲▲ | 0.58 ± 0.06 | 1.30 ± 0.05▲▲ |
| High dosage group of the composition of hemp seed oil and algal oil | 510 | 1.41 ± 0.18▲▲ | 0.73 ± 0.14▲▲ | 0.57 ± 0.05 | 1.32 ± 0.04▲▲ |

Notes:
in comparison with the blank control group, ★P < 0.05, ★★P < 0.01; in comparison with the model control group, ▲P < 0.05, ▲▲P < 0.01.

As compared to the blank control group, in the serum of rats in the model control group, the contents of TG and TC significantly increase, and the content of HDL-C significantly decreases (P<0.01 or P<0.05); as compared to the model control group, in the serum of rats in the algal group and the high, middle and low dosage groups of the composition of hemp seed oil and algal oil (with a mass ratio of 63:37), the contents of TG and TC significantly decrease, and the content of HDL-C significantly increases (P<0.01 or P<0.05); in the serum of rats in hemp seed oil group, the content of TG significantly decreases, and the content of HDL-C significantly increase (P<0.05). It is suggested that the hemp seed oil group, the algal oil group and the groups of the composition of hemp seed oil and algal oil (with a mass ratio of 63:37) have a certain hypolipidemic effect in animal model rats for hyperlipidemia. In addition, from the indicators of decreased TC and TG levels as well as increased HDL-C level in various groups, it is known that the groups of the composition of hemp seed oil and algal oil (with a mass ratio of 63:37) have significantly better hypolipidemic effect than the group of hemp seed oil monotherapy and the group of algal oil monotherapy, i.e. the composition of hemp seed oil and algal oil (with a mass ratio of 63:37) has synergistic hypolipidemic effect.

2.3 Effects on Activities of GSH-Px, MDA, SOD, and GSH in Various Groups of Rats anti-oxidation effect in animal model rats for hyperlipidemia. In addition, from the laxative levels, it is known that the groups of the composition of hemp seed oil and algal oil (with a mass ratio of 63:37) have significantly better anti-oxidation effect than the group of hemp seed oil monotherapy and the group of algal oil monotherapy, i.e. the composition of hemp seed oil and algal oil (with a mass ratio of 63:37) has synergistic anti-oxidation effect.

EXAMPLE 4

Effects on Laxative Function of Mice

1. Experimental Materials

SPF grade mice with half males and half females, body weight 18~22 g, the quality certificate for experimental animals: No. 420006000000710; License Number: SCXK (E) 2008-0005, provided by Research Center for Experimental animals, Hubei Province. The animals were raised in separate cages in SPF grade animal house at an environmental temperature of 20±2° C. and a relative humidity of 45%~70%, and fed with SPF grade mice sustaining feed, and drank sterile potable water at liberty.

Test articles: Hemp seed oil, algal oil, and composition of hemp seed oil and algal oil compounded in different mass ratios. All the test articles were dissolved in 1 mL polysorbate 80 prior to use.

TABLE 9

Comparison of activities of GSH-Px, MDA, SOD, and GSH in various groups ($\bar{x} \pm s$, n = 10)

| Groups | Dosage (mg/kg) | MDA (nmol/mL) | SOD (U/mL) | GSH (nmol/mg) | GSH-Px (U/mg) |
| --- | --- | --- | --- | --- | --- |
| Blank control group | — | 6.54 ± 0.75 | 134.98 ± 20.96 | 19.18 ± 0.69 | 117.98 ± 4.21 |
| Model control group | — | 13.61 ± 1.21★ | 85.73 ± 17.69★★ | 13.64 ± 0.47★★ | 84.21 ± 2.67★★ |
| Hemp seed oil group | 340 | 9.02 ± 1.01▲ | 98.05 ± 18.13▲ | 14.48 ± 1.01 | 95.15 ± 2.18▲ |
| Algal oil group | 340 | 8.85 ± 1.15▲ | 97.24 ± 15.47▲ | 15.96 ± 0.77▲ | 106.16 ± 4.09▲ |
| Low dosage group of the composition of hemp seed oil and algal oil | 170 | 8.97 ± 0.91▲ | 96.61 ± 20.78▲ | 15.36 ± 0.48▲ | 96.57 ± 3.02▲ |
| Middle dosage group of the composition of hemp seed oil and algal oil | 340 | 8.59 ± 0.81▲ | 101.11 ± 20.83▲▲ | 16.65 ± 0.53▲ | 104.39 ± 3.25▲ |
| High dosage group of the composition of hemp seed oil and algal oil | 510 | 7.35 ± 0.64▲ | 105.28 ± 20.83▲▲ | 18.23 ± 0.64▲▲ | 113.27 ± 3.38▲▲ |

Notes:
in comparison with the blank control group, ★P < 0.05, ★★P < 0.01; in comparison with the model control group, ▲P < 0.05, ▲▲P < 0.01.

As compared to the blank control group, in the rats of the model control group, MDA level significantly increases, and the SOD, GSH and GSH-Px levels significantly decrease (P<0.01); as compared to the model control group, in the rats of the algal oil group and the high, middle and low dosage groups of the composition of hemp seed oil and algal oil (with a mass ratio of 63:37), the content of MDA significantly decreases, and the contents of SOD, GSH and GSH-Px significantly increase (P<0.01 or P<0.05); in the rats of the hemp seed oil group, the content of MDA significantly decreases, and the contents of SOD and GSH-Px significantly increase (P<0.05). It is suggested that the groups of hemp seed oil, algal oil and the composition of hemp seed oil and algal oil (with a mass ratio of 63:37) have a certain Compound diphenoxylate tablet: purchased from Jiaozuo Boai Pharmaceutical Co., Ltd, each tablet contains 2.5 mg diphenoxylate hydrochloride and 0.025 mg atropine sulfate.

2. Experimental Methods and Results 2.1. Effects on Laxative Function of Constipated Model Mice 80 mice were taken and randomly divided into normal control group, model control group, hemp seed oil group, algal oil group and composition of hemp seed oil and algal oil in different mass ratios. The animal number in each group was 10, with half males and half females. All the groups were fasted but without water deprivation for 12 h. All the groups except the normal control group were intragastrically administered with 50 mg/Kg compound diphenoxylate tablet. After 30 min, all the groups were intragastrically administered with the test articles (see Table 10 for the dosage), and the constipation model control group and the normal control group were intragastrically administered with equal volume of normal saline. The volume for administration is 0.4 mL/10 g body weight. Each of the medicament and normal saline contains 0.2% ink. The time for the first defecation of black stool, the granule number and weight of stool within 5 hours after administration.

junction. Then it was slightly pulled into a straight line, and the whole length and the progradation distance of ink in the small intestine were measured. The ink progradation rate was calculated according to the following formula. The experimental results are shown in Table 11.

Ink progradation rate (%)=progradation distance of ink/the whole length of the small intestine×100%.

TABLE 10

Effects on defecation of constipated model mice

| Groups | Dosage (mg/kg) | The time for the first defecation of black stool (min) | The granule number of stool (granule) | Dry weigh of the stool (mg) |
|---|---|---|---|---|
| Blank control group | — | 86.19 ± 20.1 | 3.9 ± 1.5 | 0.34 ± 0.03 |
| Model control group | — | 103.53 ± 9.7$^\nabla$ | 1.5 ± 1.3$^\nabla$ | 0.11 ± 0.07$^\nabla$ |
| Hemp seed oil group | 200 | 85.05 ± 18.4* | 3.8 ± 0.8* | 0.34 ± 0.02* |
| Algal oil group | 200 | 92.62 ± 13.4* | 2.6 ± 1.4 | 0.21 ± 0.11 |
| Group of the composition of hemp seed oil and algal oil (2:7) | 200 | 90.11 ± 21.8* | 2.5 ± 0.8 | 0.22 ± 0.61 |
| Group of the composition of hemp seed oil and algal oil (47:53) | 200 | 89.01 ± 8.7* | 3.2 ± 0.3* | 0.33 ± 0.35* |
| Group of the composition of hemp seed oil and algal oil (36:64) | 200 | 84.65 ± 17.7* | 3.5 ± 0.6* | 0.34 ± 0.05* |
| Group of the composition of hemp seed oil and algal oil (6:3) | 200 | 85.79 ± 14.3* | 3.3 ± 0.9* | 0.34 ± 0.11* |

Notes:
in comparison with the model control group, *P < 0.05; in comparison with the blank control group, $^\nabla$P < 0.05.

From the results in Table 10, it can be found that as compared to the blank control group, in the model control group, the time for the first defecation of black stool delays, and the times for defecation and the dry weight of stool decrease (P<0.05). As compared to the model control group, all the hemp seed oil group and the groups of the composition of hemp seed oil and algal oil in different mass ratios can significantly decrease the time for the first defecation of black stool, and increase the granule number and dry weight of stool (P<0.05) in constipated model mice. The compositions of hemp seed oil and algal oil in different mass ratios as described in the present invention have the laxative effect on constipated model mice.

2.2. Effects on Gastrointestinal Peristalsis in Mice 80 healthy mice were taken, and randomly divided into 8 groups, with half males and half females in each group. After fasting for 20~24 h, the mice were intragastrically administered with ink (containing 5% activated carbon powder and 10% arabic gum), and then immediately intragastrically administered with the test articles respectively. The normal control group was administered with equal volume of normal saline. 30 min after the administration, the animals was sacrificed by cervical dislocation method. The mesentery was separated after the intestinal lumen was opened. The upper end of the small intestine was cut open until the pylorus, and the lower end thereof was cut to the ileocecal

TABLE 11

Effects on progradation of ink in the small intestine of mice

| Groups | Dosage (g/kg · d) | Progradation rate (100%) |
|---|---|---|
| Blank control group | — | 62.44 ± 1.03 |
| Model control group | — | 28.43 ± 4.15$^\nabla$ |
| Hemp seed oil group | 200 | 37.30 ± 5.08* |
| Algal oil group | 200 | 32.70 ± 2.15 |
| Group of the composition of hemp seed oil and algal oil (2:7) | 200 | 38.91 ± 0.83* |
| Group of the composition of hemp seed oil and algal oil (47:53) | 200 | 46.25 ± 7.42* |
| Group of the composition of hemp seed oil and algal oil (36:64) | 200 | 50.69 ± 6.30* |
| Group of the composition of hemp seed oil and algal oil (6:3) | 200 | 52.23 ± 4.67* |

Notes:
in comparison with the model control group, *P < 0.05; in comparison with the blank control group, $^\nabla$P < 0.05.

From the results in Table 11, it can be found that as compared to the blank control group, in the model control group, the ink progradation rate in small intestine of the mice of model control group significantly decreases (P<0.05). As compared to the model control group, all of the hemp seed oil group and the groups of the composition of hemp seed oil and algal oil in different mass ratios can significantly increase the ink progradation rate in the small intestine of the constipation model mice (P<0.05). It is suggested that the composition of hemp seed oil and algal oil in different mass ratios of the present invention can significantly enhance the peristalsis of the small intestine, and thus have the efficacy for promoting defecation, and all the groups of the composition of hemp seed oil and algal oil have greater ink progradation rate in the small intestine of mice than the hemp seed oil group and the algal oil group monotherapies, i.e. the composition of hemp seed oil and algal oil has synergistic effects with respect to increasing the peristalsis of small intestine.

EXAMPLE 5

Toxicity Study

1. Acute Toxicity Study

Mice were taken, and were intragastrically administered with the composition of hemp seed oil and algal oil in different mass ratios of the present invention (a. the composition of hemp seed oil and algal oil (with a mass ratio of 47:53); b. the composition of hemp seed oil and algal oil (with a mass ratio of 36:64); c. the composition of hemp seed oil and algal oil (with a mass ratio of 63:37)) at a dosage of 6 g/kg, for 4 times a day, with 6 h intervals between adjacent two times. Then, the mice was administered with normal diet, and observed for 14 consecutive days. All the organs were pathologically examined, and no organ lesion was found.

2. Long-term Toxicity Study

Mice were taken and intragastrically administered with the composition of hemp seed oil and algal oil in different mass ratios of the present invention, twice a day, for 14 consecutive days. The body weight, heart function, liver function, renal function, electrocardiogram (ECG) and other indicators were determined. The administration groups were respectively compared with the control group, and no obvious abnormality was observed. The organs of heart, liver, kidney, spleen, lung, stomach, duodenum, large intestine, small intestine, adrenal gland and genital, ect., were pathologically examined. The administration groups were respectively compared with the control group, and no obvious poisoning change was observed.

The above results suggest that the composition of hemp seed oil and algal oil in different mass ratios of the present invention is safe and nontoxic, and can be used clinically.

The invention claimed is:

1. A composition for lowering low density lipoproteins and raising high density lipoproteins in a human in need thereof consisting essentially of a therapeutically effective amount of hemp seed oil and algal oil, wherein the therapeutically effective amount is a mass ratio of 35-60:35-65 (hemp seed oil:algal oil).

2. The composition of claim 1, wherein the mass ratio of the hemp seed oil to the algal oil is 47:53, 63:37 or 36:64.

3. The composition of claim 1, wherein the algal oil consists essentially of eicosapentaenoic acid.

4. A method of lowering low density lipoproteins and raising high density lipoproteins in a human in need thereof consisting essentially of administering the composition of claim 1 to a human in need thereof.

5. The composition of claim 1, which is in the form of tablets, soft capsules, hard capsules, or granules.

6. A functional food consisting essentially of the composition of claim 1.

7. The functional food of claim 6, which is in the form of tablets, soft capsules, hard capsules, or granules.

* * * * *

UNITED STATES PATENT AND TRADEMARK OFFICE
CERTIFICATE OF CORRECTION

PATENT NO. : 10,568,919 B2
APPLICATION NO. : 15/251076
DATED : February 25, 2020
INVENTOR(S) : Zehua Chen et al.

Page 1 of 1

It is certified that error appears in the above-identified patent and that said Letters Patent is hereby corrected as shown below:

On the Title Page

Item (71) Applicant, delete the entirety of the item and replace with --INFINITUS (CHINA) COMPANY LTD., Jiang Men City (CN)-- therefor.

Item (72) Inventors, delete the entirety of the items and replace with --Zehua CHEN, Jiang Men City (CN); Jialing NING, Jiang Men City (CN); Chung Wah MA, Jiang Men City (CN); Yiting YANG, Jiang Men City (CN); Fang MA, Jiang Men City (CN)-- therefor.

Item (73) Assignee, delete the entirety of the item and replace with --INFINITUS (CHINA) COMPANY LTD., Jiang Men City, (CN)-- therefor.

Signed and Sealed this
Seventh Day of April, 2020

Andrei Iancu
*Director of the United States Patent and Trademark Office*